US012590055B2

(12) United States Patent (10) Patent No.: US 12,590,055 B2
Thiele et al. (45) Date of Patent: Mar. 31, 2026

(54) PROCESS FOR PRODUCING ISOCYANATES

(71) Applicant: BASF SE, Ludwigshafen am Rhein (DE)

(72) Inventors: Kai Thiele, Antwerp (BE); Jens Ferbitz, Ludwigshafen am Rhein (DE); Torsten Mattke, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 500 days.

(21) Appl. No.: 18/038,031

(22) PCT Filed: Nov. 23, 2021

(86) PCT No.: PCT/EP2021/082629
§ 371 (c)(1),
(2) Date: May 22, 2023

(87) PCT Pub. No.: WO2022/106716
PCT Pub. Date: May 27, 2022

(65) Prior Publication Data
US 2024/0059648 A1 Feb. 22, 2024

(30) Foreign Application Priority Data
Nov. 23, 2020 (EP) .................................... 20209343

(51) Int. Cl.
*C07C 263/10* (2006.01)
*C07C 263/20* (2006.01)
(52) U.S. Cl.
CPC .......... *C07C 263/10* (2013.01); *C07C 263/20* (2013.01)

(58) Field of Classification Search
CPC ... C07C 263/10; C07C 263/20; C07C 265/14; Y02P 20/582
See application file for complete search history.

(56) References Cited

U.S. PATENT DOCUMENTS

| | | | |
|---|---|---|---|
| 3,410,888 | A | 11/1968 | Hammond |
| 4,847,408 | A | 7/1989 | Frosch et al. |
| | | (Continued) | |

FOREIGN PATENT DOCUMENTS

| | | |
|---|---|---|
| CN | 101003497 A | 7/2007 |
| CN | 101357316 A | 2/2009 |
| | (Continued) | |

OTHER PUBLICATIONS

International Preliminary Report on Patentability received for PCT Patent Application No. PCT/EP2021/082629, mailed on Jan. 25, 2023, 6 pages.

(Continued)

*Primary Examiner* — Deborah D Carr
(74) *Attorney, Agent, or Firm* — Faegre Drinker Biddle & Reath LLP

(57) ABSTRACT

The present invention concerns a process for the preparation of isocyanates and/or polyisocyanates by reacting the corresponding amines with phosgene in a reactor, where isocyanates are obtained from a mixture of amines in gaseous or liquid form and phosgene in gaseous form, wherein no liquid solvents are used in the feeding, mixing, reacting, cooling, separating and purifying steps of the process.

17 Claims, 1 Drawing Sheet

(56) References Cited

U.S. PATENT DOCUMENTS

| | | | |
|---|---|---|---|
| 5,449,818 | A | 9/1995 | Biskup et al. |
| 6,225,497 | B1 | 5/2001 | Becker et al. |
| 8,436,204 | B2 | 5/2013 | Knoesche et al. |
| 9,533,885 | B2 | 1/2017 | Mouazer et al. |
| 10,252,912 | B2 | 4/2019 | Schelling et al. |
| 2003/0216597 | A1 | 11/2003 | Jenne et al. |
| 2004/0068137 | A1 | 4/2004 | Herold et al. |
| 2005/0020797 | A1 | 1/2005 | Pirkl et al. |
| 2005/0272910 | A1 | 12/2005 | Wolfert et al. |
| 2006/0135810 | A1 | 6/2006 | Wolfert et al. |
| 2007/0117997 | A1 | 5/2007 | Keggenhoff et al. |
| 2007/0249859 | A1 | 10/2007 | Bohm et al. |
| 2010/0137634 | A1 | 6/2010 | Ding et al. |
| 2010/0160673 | A1 | 6/2010 | Bruns et al. |
| 2018/0044179 | A1 | 2/2018 | Schelling et al. |

FOREIGN PATENT DOCUMENTS

| | | | | |
|---|---|---|---|---|
| CN | 101429138 | A | | 5/2009 |
| CN | 101429138 | B | * | 12/2011 |
| DE | 0870847 | C | | 3/1953 |
| DE | 1923214 | A1 | | 11/1970 |
| DE | 10333929 | A1 | | 2/2005 |
| DE | 102005055189 | A1 | | 5/2007 |
| EP | 0289840 | A1 | | 11/1988 |
| EP | 0570799 | A1 | | 11/1993 |
| EP | 0928785 | A1 | | 7/1999 |
| EP | 1362847 | A2 | | 11/2003 |
| EP | 1403248 | A1 | | 3/2004 |
| EP | 1451150 | A1 | | 9/2004 |
| EP | 1532107 | A1 | | 5/2005 |
| EP | 1849767 | A1 | * | 10/2007 .......... C01B 7/0706 |
| EP | 2044009 | A1 | | 4/2009 |
| EP | 2088139 | A1 | | 8/2009 |
| EP | 2199277 | A1 | | 6/2010 |
| EP | 3268349 | A1 | | 1/2018 |
| GB | 1263439 | A | | 2/1972 |
| WO | 03/45900 | A1 | | 6/2003 |
| WO | 2005/123665 | A1 | | 12/2005 |
| WO | 2007/028715 | A1 | | 3/2007 |
| WO | 2008/006775 | A1 | | 1/2008 |
| WO | 2008/055898 | A1 | | 5/2008 |
| WO | 2008/055904 | A1 | | 5/2008 |
| WO | 2009/027232 | A1 | | 3/2009 |
| WO | 2009/027234 | A1 | | 3/2009 |
| WO | 2010/010135 | A1 | | 1/2010 |
| WO | 2010/063665 | A1 | | 6/2010 |
| WO | 2010/106131 | A2 | | 9/2010 |
| WO | 2010/115908 | A2 | | 10/2010 |
| WO | 2011/018443 | A2 | | 2/2011 |
| WO | 2011/104264 | A1 | | 9/2011 |
| WO | 2013/026591 | A1 | | 2/2013 |
| WO | 2013/060836 | A1 | | 5/2013 |
| WO | 2013/079517 | A1 | | 6/2013 |
| WO | 2017/001320 | A1 | | 1/2017 |

OTHER PUBLICATIONS

International Search Report and Written Opinion received for PCT Patent Application No. PCT/EP2021/082629, mailed on Jan. 31, 2022, 8 pages.

* cited by examiner

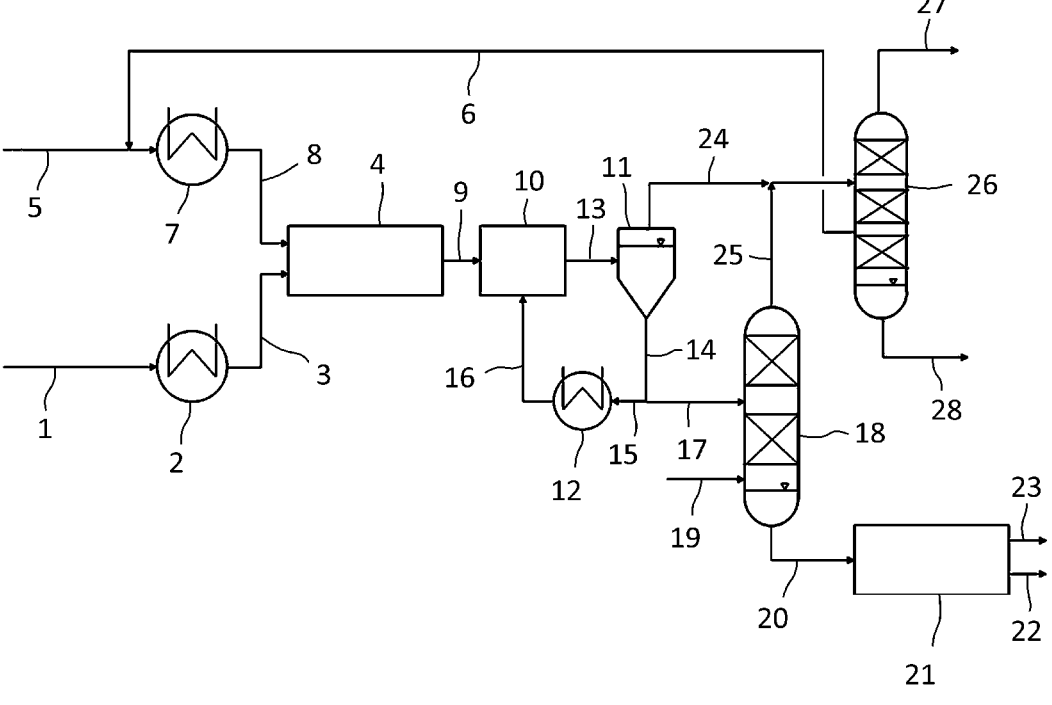

PROCESS FOR PRODUCING ISOCYANATES

CROSS-REFERENCE TO RELATED APPLICATIONS

This application is a National stage application (under 35 U.S.C. § 371) of PCT/EP2021/082629, filed Nov. 23, 2021, which claims benefit of European Application No. 20209343.1, filed Nov. 23, 2020, both of which are incorporated herein by reference in their entirety.

The present invention relates to a process for preparing isocyanates by reacting amines with phosgene.

Polyisocyanates are prepared in large quantities and serve mainly as starting materials for producing polyurethanes. They are usually prepared by reacting the corresponding amines with phosgene. Among aromatic isocyanates, methylenedi(phenyl isocyanate) (MDI) and its higher homologues and tolylene diisocyanate (TDI) have the greatest industrial importance, while among aliphatic isocyanates, hexamethylene diisocyanate (HDI) and isophorone diisocyanate (IPDI) have the greatest industrial importance.

The continuous preparation of organic isocyanates by reaction of primary organic amines with phosgene has been described many times and is carried out on a large industrial scale. The most common methods can be distinguished according to the aggregate state of the reaction feeds. In liquid phase phosgenation of aromatic diamine, a liquid stream containing amine is generally mixed with a liquid stream containing phosgene and reacted to produce the corresponding diisocyanates (e.g., Ullmann, 4th Ed. Vol. 13, p. 351).

In gas phase phosgenation, corresponding gaseous feeds are mixed, which react in the gas phase. Various embodiments of such processes are known and described for example in Ullmann, 4th Ed., Vol. 13, p. 353, or in patent documents such as DE 870847 A, EP 1532107 A, EP 0570799 A or EP 0289840 A (corresponding to U.S. Pat. No. 4,847,408 A).

Furthermore, phosgenations are known in which an amine-containing liquid stream and a gaseous phosgene-containing stream are mixed and subsequently reacted, e.g. in EP 2044009 A (corresponding to U.S. Pat. No. 8,436,204 B2), WO 2013/060836 A or WO 2013/079517 A.

A common feature of all known processes for the production of isocyanates by phosgenation is that a solvent is used at one or more steps in the overall process because the use of a solvent can increase the yield of the processes and facilitate the separation of different mixtures. For instance, solvents are used for feed streams, especially the amine-containing stream. Solvents can also be used as a quenching medium for rapid cooling of the gaseous reaction mixture in gas phase phosgenation. Solvents are also used as medium boilers in the distillation separation of high-boiling isocyanate and low-boiling HCl/phosgene mixtures or as an absorption medium for HCl/phosgene separation.

However, there are also certain disadvantages in the use of a solvent in the process: Solvent losses due to improper separation or decomposition/reaction of the solvent can occur; for example, frequently used aromatic compounds can be chlorinated with phosgene or chlorine from the dissociation of phosgene. Moreover, a contamination of reaction products with solvent residues is possible; for example, traces of chlorinated aromatic compounds can lead to an increase in the total chlorine value of PMDI. Also, the use of solvents is usually associated with lower space-time yields due to larger volume flows. In some cases considerable costs for the separation of the solvent from the product streams are incurred, both in terms of investment costs and in terms of energy costs. Solvent separation from the reactions products by distillation further leads to an additional thermal stress on the isocyanates which can reduce product yield or quality. Finally, solvents are associated with increased safety requirements due to the low flash points of common solvents.

There the technical problem underlying the present invention is to provide a novel solvent-free process for the production of isocyanates by phosgenation of the corresponding amines, which avoids the above-mentioned disadvantages associated with the use of solvent in prior art process at comparable or even lower production costs.

This technical problem is solved by the process for preparing isocyanates defined in claim 1. Preferred embodiments of the process of the invention are described in the dependent claims.

Accordingly, the present invention concerns a process for the preparation of isocyanates and/or polyisocyanates by reacting the corresponding amines with phosgene, comprising the steps of a) feeding a first reactant stream containing the amine in gaseous or liquid form, preferably in liquid form, into a reactor, b) feeding a second reactant stream containing the phosgene in gaseous form into said reactor, c) mixing and reacting said first and second reactant streams in said reactor to obtain a reaction mixture, d) cooling said reaction mixture by indirect heat transfer or by quenching with cooled reaction product to obtain a liquid reaction product, e) separating said cooled reaction mixture into a liquid reaction product containing isocyanate and a gaseous reaction product, f) purifying said liquid reaction product to obtain liquid isocyanate, and h) separating said gaseous reaction product into a first gaseous product stream essentially comprising HCl and a second liquid or gaseous product stream essentially comprising phosgene, wherein no liquid solvent is used in steps a) to f) and h).

It has surprisingly been found that the above described process can be accomplished without using liquid solvents in any of the process steps without incurring increase production costs or detrimental effects on product quality. Especially, by using indirect heat transfer methods or quenching with cooled reaction product, no liquid solvents are required in step c) which would otherwise require more sophisticated separation methods downstream. Moreover, the present invention provides for an effective purification of the liquid reaction product without using liquid medium boilers or liquid absorption media. Preferred embodiments of these purification methods will be described in more detail below.

Thus, none of the liquid solvents typically employed in the preparation of isocyanates or polyisocyanates, such as (chlorinated) aromatics like dichlorobenzene or toluene, is employed in the process of the present invention.

In one embodiment of the process of the present invention, in step a) said first reactant stream is obtained by pre-heating a liquid amine stream, optionally in the presence of an inert gas, to a desired reaction temperature.

The liquid amine stream can be partially or completely vaporized during pre-heating, i.e. it is also possible to feed the amine stream as a gaseous/liquid mixture or as a gaseous stream into the reactor.

Preferably, said gaseous second reactant stream containing phosgene is obtained by vaporizing and superheating a liquid phosgene stream to the desired reaction temperature.

In step d), said indirect heat transfer can be accomplished by guiding said reaction mixture through a heat exchanger. The heat exchanger can be cooled by any suitable gaseous or liquid cooling media.

When quenching is used as a cooling method in step d), it is preferred that cooled liquid reaction product is injected into said reaction mixture through one or more nozzles in order to obtain a thorough mixture of quenching medium and reaction mixture.

The liquid reaction product containing isocyanate obtained in step e) usually still contains residual impurities such as HCl and excess phosgene. Therefore, as a preferably initial measure in step f), the liquid reaction product is purified by separating HCl and excess phosgene from the liquid reaction product. This can, for instance, be accomplished in a stripping column using a gaseous stripping medium, for example inert stripping media such as nitrogen gas or media which fit to the overall process conditions such as gaseous HCl. During stripping, any residual carbamoyl chlorides can also be reacted to the desired isocyanates.

Preferably, step f) also comprises thermal processes to separate by-products from said liquid reaction product in order to obtain said liquid isocyanate. This can, for instance, be accomplished in a distillation column, again without using any liquid solvent.

In certain embodiments, the purification step f) further comprises separating said purified liquid isocyanate into different product fractions.

The gaseous reaction product of step e) comprises HCl and excess phosgene but may also still contain residual isocyanates and other compounds which may be compensated from the gases reaction product. Preferably, said residual isocyanates and other compounds are separated from said gases reaction product to yield a purified gaseous reaction product essentially comprising HCl and excess phosgene. Therefore, in one embodiment, the process of the present invention can comprise an optional step g) purifying said gaseous reaction product to obtain a purified gaseous reaction product essentially comprising HCl and excess phosgene.

Preferably, no liquid solvent is used in step g) either.

The process of the present invention comprises a final step h) separating the gaseous reaction product into a first gaseous product stream essentially comprising HCl and a second liquid or gaseous product stream essentially comprising phosgene.

No liquid solvent is used in step h) either.

It is usually preferred that the separation step h) is preceded by the purification step g) so that the purified gaseous reaction product essentially comprising HCl and excess phosgene is separated into a first gaseous product stream essentially comprising HCl and a second liquid or gaseous product stream essentially comprising phosgene. However, depending on process conditions and/or quality of the first and second reactant streams, purification step g) might not be necessary and the separation step h) can be performed directly after the gaseous reaction product has been obtained in separation step e).

Solvent free separation can be accomplished, for instance, via distillation, preferably distillation with vapor recompression. Using pressures up to 12-14 bar, return flow temperatures of up to −25° C. can be achieved. A suitable separation process is, for instance, described in applicant's U.S. patent Ser. No. 10/252,912B2 which involves conveying the product stream comprising HCl and phosgene into a distillation column, withdrawing at the bottom of the distillation column a phosgene-comprising stream and withdrawing at the top of the column an essentially HCl-comprising stream. A portion of the HCl-comprising stream is compressed and condensed and at least a portion the condensed liquid HCl-comprising stream is decompressed and recycled into the top of distillation column as reflux.

Also, adsorption methods can be employed. For instance, phosgene is known to adsorb on activated carbon which can then be regenerated using thermal desorption methods or desorption via pressure changes. As a further alternative, membrane separation methods can be employed. A suitable membrane separation method is, for instance described in U.S. Pat. No. 9,533,885B2 where an initial fluid stream comprising phosgene and HCl is separated into a HCl enriched and phosgene depleted gaseous stream and a HCl depleted and phosgene enriched fluid stream using a membrane separation unit.

Suitably, the gaseous reaction product is separated in step h) by at least one of distillation, membrane separation and adsorption.

Separation by distillation generally comprises the steps of conveying the gaseous reaction product into a distillation column;

withdrawing the second liquid or gaseous product stream essentially comprising phosgene as a side stream or bottoms stream from the distillation column;

withdrawing the first gaseous product stream essentially comprising hydrogen chloride as a top stream from the distillation column;

compressing at least a portion of the top stream and at least partially condensing the compressed top stream to form a liquefied stream;

decompressing at least a portion of the liquefied stream to form a cooled liquefied stream and a cooled gas stream; and recycling the cooled liquefied stream and optionally the cooled gas stream to the top of the distillation column as a reflux.

Separation by membrane separation generally comprises the steps of providing a membrane having a retentate side and a permeate side;

contacting the retentate side of the membrane with the gaseous reaction product;

withdrawing from the retentate side the second liquid or gaseous product stream essentially comprising phosgene; and withdrawing from the permeate side the first gaseous product stream essentially comprising HCl.

Separation by adsorption generally comprises the steps of providing an adsorber unit comprising an adsorbent for phosgene;

contacting the gaseous reaction product with the adsorbent to obtain an adsorbent laden with phosgene and the first gaseous product stream essentially comprising HCl;

withdrawing the first gaseous product stream essentially comprising HCl from the adsorber unit;

increasing the temperature of the laden adsorbent or decreasing the pressure in the adsorber unit to desorb phosgene from the laden adsorbent; and withdrawing the desorbed phosgene as the second gaseous product from the adsorber unit.

The adsorption and desorption steps are repeatedly cycled through.

In one embodiment of the present invention, the process for the preparation of isocyanates and/or polyisocyanates uses a phosgene feed which is obtained from a solvent free phosgene production process. Such processes are known in the art.

Thus, in a preferred embodiment of the present invention, no liquid solvent is used in the complete process chain of steps a) through h).

The second liquid or gaseous product stream essentially comprising phosgene can be partially or, preferably, completely be recycled into the reaction, specifically into the second reactant stream of step b).

Amines which can be used in the process according to the invention for the reaction to give the corresponding isocyanates are those in which the amine, the corresponding intermediates and the corresponding isocyanates are in gaseous or liquid form under the chosen reaction conditions. For gas-phase phosgenation, amines should be used which can be converted into the gas phase without significant decomposition.

Examples of isocyanates which can be obtained with the method of the present invention include aromatic di- and polyisocyanates, for example methylene diphenylene diisocyanate (mMDI) as specific isomers or as isomer mixture, polymethylene polyphenylene polyisocyanate (pMDI), mixtures of methylene diphenylene diisocyanate and polymethylene polyphenylene polyisocyanate (MDI), tolylene diisocyanate (TDI) as pure isomers or isomer mixture, isomers of xylylene diisocyanate (XDI), isomers of diisocyanatobenzene, xylene 2,6-isocyanate, naphthylene 1,5-diisocyanate (1,5-NDI), diisocyanates based on aliphatic or cycloaliphatic hydrocarbons having 2 to 18 carbon atoms, for example butane 1,4-diisocyanate, pentane 1,5-diisocyanate (PDI), hexane 1,6-diisocyanate (HDI), octane 1,8-diisocyanate, nonane 1,9-diisocyanate, decane 1,10-diisocyanate, 2,2-dimethylpentane 1,5-diisocyanate, 2-methylpentane 1,5-diisocyanate (MPDI), 2,4,4 (or 2,2,4)-trimethylhexane 1,6-diisocyanate (TMDI), cyclohexane 1,3- and 1,4-diisocyanate, 1-isocyanato-3,3,5-trimethyl-5-isocyanatomethylcyclohexane (IPDI), 2,4- or 2,6-diisocyanato-1-methylcyclohexane (H6-TDI), 1-isocyanato-1-methyl-4(3)-isocyanatomethylcyclohexane (AMCI), 1,3 (and/or 1,4)-bis(isocyanatomethyl)cyclohexane, bis(isocyanatomethyl)norbornane (NBDI), 4,4'(and/or 2,4')-diisocyanatodicyclohexylmethane, and (cyclo)aliphatic triisocyanates having up to 22 carbon atoms, for example triisocyanatocyclohexane, tris(isocyanatomethyl)cyclohexane, triisocyanatomethylcyclohexane, 1,8-diisocyanato-4-(isocyanatomethyl)octane, undecane 1,6,11-triisocyanate, 1,7-diisocyanato-4-(3-isocyanatopropyl)heptane, 1,6-diisocyanato-3-(isocyanatomethyl)hexane or 1,3,5-tris(isocyanatomethyl)cyclohexane.

Suitable amines corresponding to the above polyisocyanates are aromatic di- and polyamines, for example methylene diphenylene diamine (mMDA) as isomers or as isomer mixture, polymethylene polyphenylene polyamine (pMDA), mixtures of methylene diphenylene diamine and polymethylene polyphenylene polyamine (MDA), tolylenediamine (TDA) as pure isomers or isomer mixture, isomers of xylylenediamine (XDA), isomers of diaminobenzene, 2,6-xylidine, naphthylene-1,5-diamine (1,5-NDA), diamines based on aliphatic or cycloaliphatic hydrocarbons having 2 to 18 carbon atoms, for example 1,4-diaminobutane, 1,5-diaminopentane (PDA), 1,6-diaminohexane (HDA), 1,8-diaminooctane, 1,9-diaminononane, 1,10-diaminodecane, 2,2-dimethyl-1,5-diaminopentane, 2-methyl-1,5-pentanediamine (MPDA), 2,4,4 (or 2,2,4)-trimethyl-1,6-diaminohexane (TMDA), 1,3- and 1,4-diaminocyclohexane, 1-amino-3,3,5-trimethyl-5-aminomethylcyclohexane (IPDA), 2,4- or 2,6-diamino-1-methylcyclohexane (H6-TDA), 1-amino-1-methyl-4(3)-aminomethylcyclohexane (AMCA), 1,3 (and/or 1,4)-bis(aminomethyl)cyclohexane, bis(aminomethyl)norbornane (NBDA), 4,4'(and/or 2,4')-diaminodicyclohexylmethane, (cyclo)aliphatic triamines having up to 22 carbon atoms, for example triaminocyclohexane, tris(aminomethyl)cyclohexane, triaminomethylcyclohexane, 1,8-diamino-4-(aminomethyl)octane, undecane-1,6,11-triamine, 1,7-diamino-4-(3-aminopropyl)heptane, 1,6-diamino-3-(aminomethyl)hexane or 1,3,5-tris(aminomethyl)cyclohexane.

The present invention will now be described in more detail in connection with a preferred embodiment schematically shown in the attached figures.

BRIEF DESCRIPTION OF FIGURE

FIG. 1 is a flow diagram of a preferred process according to the invention.

As can be taken from FIG. 1, an amine-containing stream 1 is fed into the process of the present invention. The amine stream 1 is preferably provided to the process in liquid form. If the process of the present invention is preceded by a process stage in which the amine is already in gaseous form, a gaseous supply may also be used. For example, in the hydrogenation of Dinitrotoluene (DNT) to Toluenediamine (TDA), a high-boiling by-product is often separated from the amine by distillation separation and the amine is withdrawn in gaseous form.

The amine-containing stream 1 is pre-heated in a heat exchanger unit 2 to the desired temperature to yield an amine-containing first reactant stream 3 which is fed at the desired temperature to the inlet of a reactor 4. If the process of the present invention is carried out as a gas phase phosgenation, the amine stream is completely vaporized and, if necessary, superheated. As described in WO2010/010135 A, addition of an inert carrier gas or application of a vacuum can facilitate the evaporation process of the amine. If the process of the present invention is carried out as a gas/liquid phosgenation, only preheating and, if necessary, partial evaporation is required prior to feeding the first reactant stream into reactor 4.

The heat exchanger 2 can be a single-stage or multi-stage system and can use different heating media and be of a typical design known in the art. To increase energy efficiency, the heat exchanger can be integrated with other processes in the plant, for instance phosgene synthesis or with our Deacon process as described in WO2011/018443. Preheating or evaporation/superheating is advantageously carried out within a short residence time while avoiding excessively high temperatures. Suitable measures to this effect are described for instance in WO2011/104264 A.

The required preheating temperature for the gaseous or liquid amine-containing first reactant stream depends on the reaction conditions and varies with the amine and the selected reaction pressure. Temperatures in the range of 100° C. to 400° C., preferably 200 to 350° C., are usually employed for reactions with gaseous phosgene.

The phosgene-containing stream 5, obtained for instance from an up-stream phosgene production plant (not shown in FIG. 1), is supplied in gaseous or liquid form. Phosgene is usually produced by gas-phase reaction of carbon monoxide and chlorine in the presence of a solid catalyst. The gaseous reaction product can be used directly in the process. Alternatively, phosgene can be obtained after a thermal separation process where the product stream from the phosgene production process is separated from excess educts, impurities of the feeds or by-products such as $CCl_4$. If the phosgene stream is treated by condensation processes to separate low-boiling components, phosgene can also be added to the process of the present invention in liquid form, for instance via a buffer tank (not shown).

Prior to entering the reactor 4, the phosgene-containing stream 5 can be mixed in a gaseous or liquid state with a recycled phosgene-stream 6 which is obtained from excess phosgene leaving reactor 4, as will be described in more detail below. The recycled phosgene-stream 6 consists mainly of phosgene but may also include other compounds such as HCl or $CCl_4$. If necessary, both the fresh phosgene and the recycled excess-phosgene can be vaporized and/or pre-heated individually before being mixed (not shown). The phosgene-containing mixed stream is heated in a heat exchanger 7 in such a manner that a gaseous phosgene-containing second reactant stream 8 with the required reactor inlet temperatures is obtained.

The heat exchanger 7 can be single or multi-stage and, in the case of a liquid feed containing phosgene, can contain an evaporator stage. The energy supply can be realized with one or more energy sources. In addition to liquid and gaseous energy sources such as steam, condensate or rolling gas, electrical heating is also possible. In the context of the present invention, all types of heat exchangers or electric heaters known in the art can be employed. To avoid thermal decomposition of phosgene in the heat exchanger, long residence times at high temperatures as well as high wall temperatures may have to be avoided, as described for instance in WO 2010/106131 A.

The required pre-heating temperature for the gaseous phosgene-containing second reactant stream 8 depends on the reaction conditions and varies with the amine and the selected reaction pressure. Temperatures in the range of 100° C. to 400° C., preferably 200 to 350° C., are usually employed for reactions with gaseous phosgene.

The first and second reactant streams 3, 8 are fed in their pre-heated state into the reactor 4. In the reactor 4, which may be the reactor system having a multi-stage design, mixing and reacting the reactant streams is carried out.

At the outlet of the reactor 4, at least 95%, preferably to at least 98%, particularly preferably to at least 99% of amine groups of the supplied first reactant stream have been reacted to obtain a reaction mixture stream 9 comprising the desired isocyanates. In addition to the desired isocyanates, the reaction mixture stream 9 further comprises intermediate products such as carbamoyl chlorides or by-products such as amine hydrochlorides, ureas, biuretes, carbodiimides, uretonimines, uretdiones and isocyanurates.

Preferably, the reaction is conducted at an stoichiometric excess of phosgene, preferably in the range of 1% to 500%, more preferably between 5 and 400% and especially preferably between 10 and 300%.

The reaction conditions are selected such that the formation of solid intermediates and by-products such as amine hydrochlorides and urea is minimized or largely avoided. This may require correspondingly high reaction temperatures and low pressure. The reaction temperatures are usually selected in the range of 200 to 600° C., preferably between 250 and 500° C. The pressure in the reactor 4 is preferably between 0.1 and 10 bara (bar absolute), preferably between 0.2 and 5 bara, especially preferably between 0.5 and 3.5 bara.

Reactor 4 may comprise a separate mixing device and one or more residence time devices. In some embodiments additional streams can be supplied to the reactor system. For example, WO 2009/027232 A describes the supply of a separate inert gas stream to prevent fouling in the mixing device. In WO 2013/079517 A a solid is fed into the reactor as a fluidized material.

A first reactant stream 3 comprising liquid amine is preferably supplied to the reactor 4 via nozzles. EP 2044009 A describes suitable spray nozzles for this purpose to produce fine droplets. Nozzles for feeding amine to the reactor are also described in WO 2013/060836 A or WO 2013/079517 A. One or more nozzles can be employed to provide an equal distribution of the amine-containing first reactant stream within the reactor 4.

The reactor 4 may comprise one or more mixers. For instance, gaseous reactants such as a first reactant stream 3 comprising gaseous amine can be supplied to the reactor 4 via static mixers. Typical mixer designs are described in EP 1319655 A, EP 1362847 A, EP 2088139 A, CN 101357316 A, WO 2007/028715 A, WO 2008/055898 A, WO 2009/027232 A, WO 2009/027234 A or WO 2010/010135 A. In addition or alternatively, the reactor 4 can be provided with dynamic mixers, as for instance described in EP 2199277 A, or with micro-structured mixers as described in EP 0928785 A.

Downstream of the inlet of the amine-containing first reactant stream into the reactor 4, the first reactant stream is brought into contact with the gaseous, phosgene-containing second reactant stream and are reactant mixture is created. The reactant mixture reacts in a subsequent reaction chamber.

When configured as a reactor system, reactor 4 can comprise one or more reactors arranged in series and/or parallel. Preferably, these reactors are configured as cylindrical reaction chambers, in which a turbulent reactant flow is generated as, for instance, described in EP 0289840 A. Reaction chambers with non-circular cross sections can also be employed, as for instance, described in EP 1451150 A. Generally, all known reactor types suitable for gas phase reactions and gas/liquid reactions can be used in the context of the present invention, such as tubular reactors, columns, spray towers, etc. Further, in combination with an inert solid phase, fluidized bed reactors, rotary kilns or rotating bed reactors can also be used. Preferably, reactors which have a narrow residence time distribution and thus low backmixing or few dead zones are employed for carrying out the process of the present invention.

The chemical reaction of amines with phosgene is generally exothermic. The reaction is preferably performed under adiabatic conditions. In certain cases, it can be necessary to heat the reactor. In other cases, cooling of the reactor up to isothermal operation can also be a feasible option.

After conversion of the amine groups, the reaction mixture 9 obtained at the outlet of reactor 4 is rapidly cooled down to avoid secondary and/or subsequent reactions. In the preferred embodiment of the process of the present invention as shown in FIG. 1, cooling of the reaction mixture 9 is carried out by means of a quenching system comprising a quench system 10, a phase separator 11 and a heat exchanger 12. In the quench system 10, the reaction mixture 9 is quenched by injection of a liquid reaction product of the present process itself which has been supercooled in heat exchanger 12. This results in a gas phase containing preferably low-boiling components such as HCl and excess phosgene and a liquid phase containing the isocyanate formed and optionally, intermediate and secondary products. The mixed liquid gas phases 13 are separated in phase separator 11. At least a part 15 of the removed liquid phase 14 is supercooled in heat exchanger 12 and used as quenching medium 16 in quench system 10 as described above. Various alternative designs for the quench system are conceivable. Usually the liquid quenching medium 16 is sprayed through one or more spray nozzles and brought into contact with the reaction mixture 9. EP 1403248 A describes a cylindrical quench zone with spray nozzles distributed around the circumference. In WO 2008/055904 A, the quench nozzles are located in the interior and provide a complete curtain of quench drops.

The quench system 10 can also be integrated directly into the reactor 4, for instance in the form of a quench zone or be accommodated within an apparatus together with the last reaction stage. The connection between reaction stage and quench stage can be designed in suitable, technically feasible way. Preferably, the quench zone is configured within the same cylindrical apparatus. If necessary, a constricted area (as described in WO2005/123665 A) or a permanent constriction (as described in WO 2005/123665 A) can be located between the reaction zone and quench zone. In addition, baffles can be provided between the reaction zone and the quench zone. To avoid deposits in the quench zone, the quench medium can be advantageously guided as a counter-current to the flow-direction of the reaction mixture. To this effect, wetting of the walls can also be contemplated, as described, for instance, in WO 2010/115908 A. In this event, wetting should also be accomplished using supercooled, liquid reaction product. Optionally, such a wetting can also be provided for the reaction zone in order to avoid deposits, especially if the reaction zone and quench zone are located in a cylindrical apparatus. In the quench system 10, the reaction mixture 9 is cooled from the reactor outlet temperature to temperatures in the range of 50 to 250° C., preferably 80 to 200° C.

The purpose of phase separator 11 is to separate the gaseous reaction products from the liquid products in the product mixture 9. The phase separation can be carried out in one or more stages. Preferably the phase separation in the first stage uses gravity separation. The separation can be realized together with a reaction zone and the quench zone in one apparatus. Here the liquid collects in a sump and forms an interface to the gas phase. This can be discharged from the side or top of the apparatus. As an alternative to gravity separation, however, any principles of liquid-gas separation such as cyclones or centrifuges can also be used. The separated gas phase from an initial phase separation, e.g. gravity separation, can also entrain drops of the liquid phase (entrainment). This applies in particular to fine droplets (aerosols). All suitable separator types such as demisters, lamella separators, Venturi scrubbers or aerosol filters can be used for their separation.

A part 15 of the liquid phase 14 from phase separator 11 is fed to heat exchanger 12 which, as described above, is used to super-cool the liquid phase to provide the super-cooled quenching medium 16. The heat exchanger 12 is preferably designed as a single-stage system, although a multi-stage design are also feasible. The heat exchanger can be of any type suitable for the cooling of liquids, e.g. shell-and-tube heat exchanger, plate heat exchanger or spiral heat exchanger.

The quantity of quench liquid required depends on the reaction system, the reactor outlet temperature, the targeted cooling in the quench stage and the degree of super-cooling in the heat exchanger 12. Preferably, the outlet temperature of the supra-cooled liquid 16 leaving the heat exchanger 12 is in the range from 1 and 100 K below the targeted quench outlet temperature, especially preferably between 5 and 80 K and especially preferably between 10 and 60 K.

Any suitable cooling medium such as water or air can be used in the heat exchanger 12. Preferably, boiling cooling with water as a cooling medium is implied on the coolant side of the heat exchanger. The steam obtained in this way can then be used for other energetic purposes if necessary. A direct or indirect energy integration with the preheating of the reactant streams is also conceivable.

In some embodiments, it may be necessary to provide for a pressure increase for the liquid phase in the circuit from the outlet of phase separator 11, via heat exchanger 12 quench system 10 to overcome height differences and pressure losses and to generate the necessary inlet pressure for the spray nozzles of the quench system. Such pressure increase can be accomplished by a pump (not depicted in FIG. 1). Any suitable type of pump can be used for this purpose. Moreover, filters can be provided in this circuit for the separation of solids, as described in WO 2010063665 A, to avoid fouling and clogging problems in the pump, the heat exchanger or the quench nozzles.

A part 17 of the liquid product 14 which is not led to the heat exchanger 12 essentially contains the desired isocyanate, carbamoyl chlorides of the isocyanate as intermediate products, typical high-boiling by-products and secondary products and a small amount of dissolved phosgene or hydrogen chloride. The removal of dissolved phosgene and HCl and the cleavage of any carbamoyl chlorides present is typically performed in a stripping column 18. In addition, interconnected columns, or several aerators/phase separators can also be employed. In particular, the splitting of carbamoyl chlorides sometimes requires sufficient residence times.

Stripping gas 19 is usually led into the bottom of the column 18. It is also possible to use several stripping gases. For example, HCl can be dosed above the sump to remove traces of phosgene, while in the sump an inert such as N2 is used to remove the dissolved HCl. But other combinations of stripping gases or dosages are also possible. The stripping effect can be supported by heating the sump or by partial evaporation of sump product. Depending on the product, it may also make sense to create a steam flow exclusively by partial evaporation. For many high-boiling isocyanates, however, the stripping gas variant is advantageous to avoid high sump temperatures.

If the column 18 is operated as a pure stripping column, the liquid stream 17 is led directly into the head of the column. For the removal of isocyanate from the gas phase it can be useful to provide a reinforcement part. The reflux can then be obtained by partial condensation. Alternatively, cooled sump product can serve as reflux.

The sump temperature of the stripping column should be less than 250° C. and preferably less than 200° C. to avoid generation of secondary products. The pressure is preferably in the range of 0.1 to 5 bara, more preferably in the range of 0.5 to 3.5 bara.

The largely HCl- and phosgene-free, mainly isocyanate-containing bottom product 20 can be directed to a further purification or separation stage 21 if necessary to obtain a an essentially pure isocyanate stream 22 and one or more streams 23 comprising separated impurities and residual compounds. If necessary, thermal dechlorination can be carried out, in which in particular phosgene storage compounds such as chloroformamidines are reacted to release phosgene. Distillable isocyanates (e.g. TDI or HDI) are often thermally processed in a single or multi-stage purification process, in particular to remove high-boiling residues and, if necessary, low-boiling components. Possible concepts are described for example in U.S. Pat. No. 3,410,888 A or US 2006/0135810 A. For an isomeric and oligomeric mixture of methylenediphenyl diisocyanates (MDI), the separation of 2-core isomers (in different purities and mixtures) from polymeric MDI (PMDI) is also known and described, for example in DE 1923214 A, DE 102005004 A, DE 102005055189 A, CN 101003497 A or DE 10333929 A.

The gaseous streams 24, 25 from phase separator 11 and stripping column 18, respectively, consist mainly of the produced HCl and the excess phosgene and are then generally fed to a HCl/phosgene separation system 26. However, the case of very small phosgene excess, this additional separation stage can be dispensed with. If necessary, the streams 24, 25 are cooled down again prior to the HCl/phosgene separation stage and, if necessary, partially condensed (not depicted in FIG. 1). In this way, any heavier-boiling components still contained can be condensed or desublimated and thus a purification of the HCl/phosgene stream can be accomplished. If necessary, the condensed phase can be returned to the reaction column or to the quench system or a purge can be drawn and sent to destruction. In this way, the leveling of medium-boiling secondary components such as $CCl_4$ (stemming from phosgene synthesis) can be avoided.

The actual HCl/phosgene separation system 26 can preferably be accomplished by distillation. Alternatively, membrane-based separation systems (as described, for instance, in WO 2013/026591 A) can also be employed. As yet a further alternative, adsorption-based separation systems, using for instance activated carbon, can be employed.

FIG. 1 shows a HCl/phosgene separation system 26 configured for a distillation separation in which a gas phase 27 containing mainly HCl is removed overhead. In a side discharge, a gaseous or liquid phase 6, mainly containing phosgene, can be removed and returned to the second reactant stream, as described above, optionally after compression. In the sump of the HCl/phosgene separation system 26, higher-boiling components 28 could be led to a disposal or back into the quench circuit or the reaction column.

Alternatively, the medium-boiler separation HCl/phosgene separation system 26 can be dispensed with and the phosgene-enriched streams 6 can then be drawn directly from the sump. Optionally, energy input in the sump via evaporators may be required.

The reflux at the top of the column can be obtained by partial condensation of the gas phase 27. To avoid too low temperatures during condensation, it can be advantageous to compress the streams 24 and 25 before introduction into the HCl/phosgene separation column 26, if necessary after partial condensation, and thus to carry out the distillation at a higher pressure than the reaction system (see also WO 2017001320 A). Alternatively, the stream 27, which contains primarily HCl, can be compressed, partially condensed and the condensate then expanded into the column head (see, for instance, EP 3268349 A).

The above description should be construed as an example with possible options. However, it also includes all options not specifically mentioned for individual plant components, provided that they meet the requirement for solvent-free operation. Furthermore, individual plant components arranged in parallel in order to increase the availability of the plant or to facilitate plant control, especially during partial load operation.

The process described in the present claims and description pertains at least to the steady-state operation of the process for the preparation of isocyanates and/or polyisocyanates. It is explicitly not excluded that an inert solvent may be used under conditions outside the normal plant operation, e.g. for rinsing processes or during start-up processes preceding the steady-state operation or shut-down processes following the steady-state operation.

The invention claimed is:

1. Process for the preparation of isocyanates or polyisocyanates by reacting the corresponding amines with phosgene, comprising the steps of
   a) feeding a first reactant stream containing the amine in gaseous or liquid form into a reactor,
   b) feeding a second reactant stream containing the phosgene in gaseous form into said reactor,
   c) mixing and reacting said first and second reactant streams in said reactor to obtain a reaction mixture,
   d) cooling said reaction mixture by indirect heat transfer or by quenching with cooled reaction product to obtain a liquid reaction product,
   e) separating said cooled reaction mixture into a liquid reaction product containing isocyanate and a gaseous reaction product,
   f) purifying said liquid reaction product to obtain liquid isocyanate, and
   h) separating said gaseous reaction product into a first gaseous product stream essentially comprising HCl and a second liquid or gaseous product stream essentially comprising phosgene,
   wherein no liquid solvent is used in steps a) to f) and h).

2. The process of claim 1, wherein, in step a) said first reactant stream is obtained by pre-heating a liquid amine stream, optionally in the presence of an inert gas, to a desired reaction temperature.

3. The process of claim 2, wherein said liquid amine stream is partially or completely vaporized during pre-heating.

4. The process of claim 1, wherein said gaseous second reactant stream containing phosgene is obtained by vaporizing and superheating a liquid phosgene stream to the desired reaction temperature.

5. The process of claim 1, wherein, in step d) said indirect heat transfer is accomplished by guiding said reaction mixture through a heat exchanger.

6. The process of claim 1, wherein, in step d) said quenching is accomplished by injecting said cooled reaction product into said reaction mixture through one or more nozzles.

7. The process of claim 1, wherein step f) comprises separating HCl and excess phosgene from said liquid reaction product.

8. The process of claim 7, wherein HCl and excess phosgene are separated from said liquid reaction product using a gaseous stripping medium, selected from inert gaseous stripping media or gaseous stripping media fitting to the process conditions, especially HCl.

9. The process of claim 1, wherein step f) comprises thermal processes to separate by-products from said liquid reaction product in order to obtain said liquid isocyanate.

10. The process of claim 7, wherein step f) further comprises separating said purified liquid isocyanate into different product fractions.

11. The process of claim 1, wherein said process, prior to step h), further comprises the step
    g) purifying said gaseous reaction product to obtain a purified gaseous reaction product essentially comprising HCl and excess phosgene.

12. The process of claim 11, wherein no liquid solvent is used in step g).

13. The process of claim 1, wherein said second liquid or gaseous product stream is partially or completely recycled into said second reactant stream.

14. The process of claim 1, wherein the gaseous reaction product is separated in step h) by at least one of distillation, membrane separation and adsorption.

15. The process of claim 14, wherein separation by distillation comprises the steps of conveying the gaseous reaction product into a distillation column;

withdrawing the second liquid or gaseous product stream essentially comprising phosgene as a side stream or bottoms stream from the distillation column;

withdrawing the first gaseous product stream essentially comprising hydrogen chloride as a top stream from the distillation column;

compressing at least a portion of the top stream and at least partially condensing the compressed top stream to form a liquefied stream;

decompressing at least a portion of the liquefied stream to form a cooled liquefied stream and a cooled gas stream; and recycling the cooled liquefied stream and optionally the cooled gas stream to the top of the distillation column as a reflux.

16. The process of claim 14, wherein separation by membrane separation comprises the steps of providing a membrane having a retentate side and a permeate side;

contacting the retentate side of the membrane with the gaseous reaction product;

withdrawing from the retentate side the second liquid or gaseous product stream essentially comprising phosgene; and withdrawing from the permeate side the first gaseous product stream essentially comprising HCl.

17. The process of claim 14, wherein separation by adsorption comprises the steps of providing an adsorber unit comprising an adsorbent for phosgene;

contacting the gaseous reaction product with the adsorbent to obtain an adsorbent laden with phosgene and the first gaseous product stream essentially comprising HCl;

withdrawing the first gaseous product stream essentially comprising HCl from the adsorber unit;

increasing the temperature of the laden adsorbent or decreasing the pressure in the adsorber unit to desorb phosgene from the laden adsorbent; and withdrawing the desorbed phosgene as the second gaseous product from the adsorber unit.

* * * * *